United States Patent [19]

Sweeny

[11] Patent Number: 4,756,906

[45] Date of Patent: Jul. 12, 1988

[54] COSMETIC COLORANT COMPOSITIONS

[75] Inventor: Norman P. Sweeny, North Oaks, Minn.

[73] Assignee: Minnesota Mining and Manufacturing Company, St. Paul, Minn.

[21] Appl. No.: 21,911

[22] Filed: Mar. 4, 1987

Related U.S. Application Data

[63] Continuation-in-part of Ser. No. 840,917, Mar. 18, 1986, abandoned.

[51] Int. Cl.⁴ .................. A61K 7/021; A61K 7/025; B05D 3/12
[52] U.S. Cl. ...................... 424/63; 424/64; 427/369; 514/844
[58] Field of Search .............. 424/63, 64; 427/369; 514/844

[56] References Cited

U.S. PATENT DOCUMENTS 3,947,571  3/1976  Murphy et al. ............... 424/64
4,217,344  8/1980  Vanlerberghe ............... 424/60
4,450,221  5/1984  Terada et al. ................ 430/106.6

FOREIGN PATENT DOCUMENTS 6049312  9/1979  Japan .
56-49312  5/1981  Japan .

OTHER PUBLICATIONS

Kirk-Othmer "Encyclopedia of Chemical Technology", 3rd Ed., vol. 6, pp. 121-128.

Primary Examiner—Joseph L. Schofer
Assistant Examiner—Peter F. Kulkosky
Attorney, Agent, or Firm—Donald M. Sell; James A. Smith; Mark A. Litman

[57] ABSTRACT

Cosmetic compositions are provided which have modifiable color characteristics. A single composition may be applied, and with the application of pressure, the color of the composition may be changed. The composition contains a first pigment and mircocapsules containing a second pigment. Upon rupture of the microcapsules, the coloration of the second pigment is added to the composition, altering its color characteristics.

15 Claims, No Drawings

COSMETIC COLORANT COMPOSITIONS

"This application is a CIP of Ser. No. 840,917 filed Mar. 18, 1986 and now abandoned"

BACKGROUND OF THE INVENTION

1. Field of the Invention

The present invention relates to compositions useful in the application of colored cosmetics to the human body.

2. Background of the Art

The application of decorative or masking colors to the skin of humans and particularly to the face of humans is a highly specialized technical area. Compositions vary greatly depending upon the specific location to which the color is to be applied. The compositions used to apply color to the lips (e.g., lipstick or lip balm) require water repellancy because of their repeated contact with liquids. Mascara must have very high color density and strong bonding ability to eyelashes. Rouge, blusher and pancake must be very fine and easily spreadable. Eye shadow must also be fine and spreadable, yet should not break down during mild abrasion as.is encountered with repeated blinking and movement of the eyelids. There are also bases and foundations for colors which require specific properties to enable them to perform their unique function.

In recent years, styles have become more dramatic, allowing the use of more color and even multiple colors in the applications of makeup. For example, one portion of an eyelid may be pink and another portion blue. The change in colors can be used not only for the multicolor appearance, but the change can give an appearance of eyes being farther apart or closer together then they actually are. Such makeover techniques are highly valued by the cosmetician and makeup artist.

There are some problems involved in blending colors, however. Even though separate color sources and separate brushes may be used to apply the individual colors, the later applied colors will always contact the first applied colors. The brushes will then pick up colorant from the skin and transport it back to the color source. The brushes themselves will also retain mixtures of colors, rendering them less useful. The intermixing of colors in the original source will of course diminish the quality of the colorant.

It is fairly common to find encapsulated liquid materials in the marketplace. Technology has been available for many years to effectively provide microcapsules with liquid oleophilic ingredients. Representative processes are shown in U.S. Pat. Nos. 3,016,308 and 3,516,941. These patents disclose in situ polymerization reactions in which a hydrophobic oil phase is dispersed in an aqueous phase containing resin precursors, particularly aminoplast resin precursors (to form urea/aldehyde resins and the like). High shear agitation is used to keep the capsule size small. Addition of an acid catalyst initiates the polycondensation of the aminoplast precursors, resulting in the deposition of the aminoplast resin about the dispersed droplets of the oil phase. This produces the microcapsules.

Other polycondensation encapsulation techniques are shown in U.S. Pat. Nos. 3,429,827 and 4,000,087. These particular techniques are more limited in the classes of hydrophobic inner phases acceptable in the microcapsules because of reaction with the oil soluble monomer or poor solubility of the monomer in the desired hydrophobic phase.

U.S. Pat. No. 3,930,101 teaches that, to be retained in the hydrophobic phase during high shear dispersion of a fluid particulate dispersion, it is necessary that the particulate be preferentially wetted by the hyrophobic phase. It is suggested to use suitable surfactants which adsorb to the particulate surface as a way to achieve the desired preferential wetting. It has, however, been recognized that, in the in situ polymerization of aminoplast resins method for encapsulation, the presence of surfactants interferes with the deposition of the aminoplast resin at the hydrophobic phase/water phase interface, giving poorly formed or leaky capsules. Similarly, oil soluble suspending agents could alter the wetting of many particulates. Since many of these materials contain carboxylate groups, exposure to highly acidic medias often converts them to carboxylic acid groups altering their adsorbability to the particulates.

U.S. Pat. No. 4,307,169 teaches the inclusion of magnetic materials into a pressure fixable core material within a shell formed by interfacial polycondensation.

U.S. Pat. No. 3,954,666 teaches the preparation of semipermeable microcapsules containing catalysts and ferromagnetic materials.

U.S. Pat. No. 4,450,221 teaches magnetic toners comprising lyophilic magnetic particles and a resin surrounded by a resin wall to form microcapsules. Colorants such as pigments or dyes may be included in the wall forming resin or the toner. The magnetic particles are rendered lyophilic by treatment with a titanate or silane coupling agent. The coupling agent is said to uniformly disperse the particles in the binder resin and firmly bond the magnetic particle to the resin.

BRIEF DESCRIPTION OF THE INVENTION

Conventional cosmetic formulations, with or without a predominant coloration in the composition, can be rendered colored, can be highlighted, or can be altered in color by the application of pressure to the composition after or during application. The presence within the composition of frangible microcapsules containing light-stable dyes or pigment enables this coloring phenomenon to occur.

Color adjustable cosmetic compositions comprise a first colorant, a binder, and a frangible microcapsule comprising a shell, an encapsulated liquid and a second light-stable colorant which differs in color from said first colorant.

DETAILED DESCRIPTION OF THE INVENTION

The present invention relates to cosmetic formulations, with or without a predominant coloration in the compositions, which by the application of differential pressure over the surface of the composition, during or after application, can be rendered colored, can be highlighted, or can be altered in its predominant color. Conventional cosmetic color compositions such as eye shadow, lipstick, pancake, face powder, lip balm, cream rouge, mask powder, suntan lotion, and the like are used as the basic compositions of the invention. To these basic compositions are added microcapsules containing light-stable dyes or pigments of colors (including sparkling pigments) which may be different from the color in the original composition. After application of the composition, further light rubbing (as with a finger) will rupture the microcapsules, highlighting or changing the color in the area where the composition was rubbed by exposing the encapsulated pigment within the composition.

In accordance with the present invention, microcapsules are prepared by in situ such as aminoplast polymerization. The techniques disclosed, generally referred to as an in situ polymerization reaction, yield, for example, an aminoplast resin capsule wall material. In the process, a hydrophobic oil phase is dispersed in an aqueous phase containing the aminoplast resin precursors by applying high shear agitation. Addition of an acid catalyst initiates the polycondensation of the aminoplast precursors, resulting in the deposition of the aminoplast resin about the dispersed droplets of the oil phase, producing the microcapsules.

Pigments of various types, when dispersed in water insoluble oils, and then mixed or dispersed under high shear into water phases to produce oil in water dispersions, will show a variety of behaviours depending upon the surface characteristics of the pigment particles relative to the oil and water phases. In particular, pigment particles which are wetted by the water phase and incompletely or poorly wetted by the oil phase, will readily move from the oil phase to the water phase during this dispersion process. Attempts to encapsulate such a pigment will generally be unsuccessful and lead to a capsule containing few, if any, pigment particles. Pigment particles which are completely wetted by the oil phase and incompletely or poorly wetted by the water phase will tend to remain in the interior of the oil phase droplets during the dispersion process. Pigment particles of this type will generally result in microcapsules having the pigment particles in the oil core of the microcapsule with relatively few particles being abstracted from the oil phase or caught or immobilized in the microcapsule shell wall. Finally, pigment particles which are incompletely wetted by either the oil phase or by the water phase will be found concentrated at the oil/water interface during such a dispersion process. Microcapsules formed from this type of pigment will give capsules having the pigment particles more or less in the shell wall of the microcapsule. The ability to alter the surface characteristics and more particularly the wetting characteristics of pigment particles relative to the chosen oil and water phase compositions provides the means to control the encapsulatability of pigment dispersions and the means to control the ultimate location of the majority of the pigment particles within the microcapsule (i.e., either freely dispersed in the core oil phase or fixed at or within the microcapsule shell wall). Useful products can be made from microcapsules containing pigments of either of the two types.

The term "light-stable" as used in the practice of the present invention means that the dye or pigment does not visually observably change color when lighting conditions change (e.g., from indoor to outdoor lighting, or with change of wavelength irradiation such as to infrared exposure) or after short term exposure (e.g., at least 15 minutes) to sunlight. This parameter is important because random color changes according to lighting conditions would be undesirable. Furthermore, the use of photochromic dyes such as those described in Japanese Patent Publication No. J5649312 are highly undesirable because of both toxicity and the need to keep them in solution. This latter condition is essential with photochromic dyes as their repeatable color changes only occur in solution. Furthermore, the chemical activitiy of the dyes necessary to render them photochromic makes the dyes less than desirable in direct skin applications. Additionally, according to that Japanese Patent Publication, the microcapsules would not be frangible as this would destroy their photochromic capability. Also, the optical color change effect is minimized by the strong walls of the capsules and the low optical effect producible by the dyes from only within the capsules.

It is part of this invention that the second colorant be associated with the microcapsules. This means that the second colorant should be on the shell, in the shell, or within the shell of the microcapsule. The more of the second pigment that is within the shell, the greater will be the degree change in the overall coloration of the product upon rupture of the shells. That is because any second pigment (colorant) on the exterior of the shell will contribute to the overall color of the composition before rupture of the microcapsules. It is therefore preferred that said second colorant is predominantly encapsulated by the shell. This means that at least 50% by weight of said second colorant is within the shell. Amounts as small as 25% by weight of said second colorant within the capsules (in the shell wall and inside the shell itself) can significantly alter the color or tone of the composition on being ruptured. It is preferred that at least 50% by weight of all second colorant be inside the shell (on the wall, or in the liquid carrying medium, or in the wall). More preferably at least 70% is inside the shell, and most preferably more than 90% of said second colorant is inside the shell.

The preferred method of forming capsules for use in the present invention is a process whereby the surface of non-magnetic colorant particulates, by the addition of surface adsorbable agents, are rendered oleophilic and can maintain their oleophilicity in water (at pH's encountered in encapsulation processes). This may mean pH's of 10 or more for some interfacial encapsulation processes or pH 4–1.8 for in-situ aminoplast encapsulation. The additive must remain on the surface of the particle for a period of at least five minutes at a pH representative of the most extreme pH to be encountered in the encapsulation process under the following conditions:

1. The oil phase used as the interior phase of the capsule (e.g., diethyl phthalate) is placed in the same flask with the pigment. The pigment is either pretreated with the additive or the pigment is treated in-situ by incorporation of additive into the oil phase.

2. One part of the oil phase dispersion to ten parts of an aqueous phase at the required pH are combined in a flask.

3. The combination in the flask is shaken vigorously for at least five (and preferably ten) minutes. The phases are microscopically examined to determine the location of the pigment. If at least 20%, preferably no more than at least 10%, and no more than at least 5% of the pigment is in the water phase (unassociated with oil phase), the additive has failed.

This test procedure defines the functional ability of an oleophilic additive according to the present invention. Any material that passes this test (no more than 20% in the water phase) is referred to as a functional oleophilic additive.

It has been found that two main classes of pigment surface modifying agents are particularly useful for controlling the wetting characteristics of a variety of pigment types. These materials are usually described as titanate or silane coupling agents. Judicious selection of the coupling agents from these classes allows the control of the encapsulatability and particulate location of a variety of pigment types, associated with a variety of different oil phase compositions. Three methods for the use of these surface modifying agents are possible depending upon the specific agent chosen and on other restrictions dictated by the microcapsule use. They are:

1. Pretreatment of the pigment particles prior to dispersion in the oil phase.
2. Addition of the coupling agent directly to the oil phase of the pigment dispersion.
3. Having the coupling agent present in the water phase at the time of dispersing of the oil/pigment dispersion.

The first process is the most universally useful as the pretreatments are usually accomplished by exposure of the pigments to solutions of the coupling agents. Selection of solvents according to the nature of the coupling agent is more readily accomplished. For example, the preferred solvent, and sometimes the required solvent, for use with many of the silane coupling agents is water. In other cases, the solubility of a chosen coupling agent in the desired oil phase for encapsulation may not be satisfactory for effective pigment treatment, or it may be undesirable to have free coupling agent present in the oil phase of the encapsulated pigment dispersion. Treatment of the pigment in solutions of 0.05% to 10% of the coupling agent will usually produce acceptable results, with 0.25% to 2.0% being most desirable.

The second method is restricted to coupling agents of the two classes that have solubility in the oil phase composition to be used in the microcapsule. Usually an excess of the coupling agent over that necessary for the surface treatment of the pigment will be used. This will result in some residual soluble coupling agent present in the oil/pigment dispersion. The addition of 0.05% to 5% by weight of the particulate will usually produce acceptable results.

The third method is restricted to those coupling agents which are soluble in water. It is most useful with pigments which are wettable by water. Additions of 0.05% to 10% of the coupling agent by weight of the particulate will usually produce acceptable results, with 0.25% to 2.0% being the most desired range.

Pigments as used in the present invention refer exclusively to solid materials. Dyes or pigments carried in solid polymeric or waxy phases can constitute pigments in the present invention, but dyes dissolved in liquid media are not solids and therefore not within the definition of pigments.

Chemisorption of the additives to the particulates is preferred, but not essential. Adsorption of the additives to the particulates (e.g., pigments) by Van der Waals forces, dipole-dipole attraction, or hydrogen bonding are also useful. Chemisorption requires an actual chemical bond to be formed between a part of the additive and the particulate surface. The pigments for which this process is most useful are those which have hydrophilic surfaces initially and require increased oleophilicity of their surfaces. The pigments may be a single, solid particulate, colorant materials carried in a solid medium or colloidal materials which in gross or bulk form appear gelatinous (e.g., colloidal, hydrated iron oxide) and thus act as a solid.

Titanate coupling agents that are illustrative of those used in the present invention as agents to modify the wettability of the particulates have formulas shown in Table I.

TABLE I

1. Isopropyl triisostearoyl titanate
2. Isopropyl methacryl diisostearoyl titanate
3. Isopropyl dimethacryl isostearoyl titanate
4. Isopropyl tridodecylbenzenesulfonyl titanate
5. Isopropyl diacryl isostearoyl titanate
6. Isopropyl tri(dioctylphosphato) titanate
7. Isopropyl 4-aminobenzenesulfonyl di(dodecylbenzenesulfonyl) titanate
8. Isopropyl trimethacryl titanate
9. Isopropyl tricumylphenyl titanate
10. Isopropyl di(4-aminobenzoyl) isostearoyl titanate
11. Isopropyl tri(dioctylpyrophosphato) titanate
12. Isopropyl triacryl titanate
13. Isopropyl tri(N ethylamino-ethylamino) titanate
14. Isopropyl tri(2-aminobenzoyl) titanate
15. Isopropyl tri(butyl, octyl pyrophosphato) titanate di(dioctyl, hydrogen) phosphate
16. Di(butyl, methyl pyrophosphato) isopropyl titanate di(dioctyl, hydrogen) phosphite
17. Titanium isostearate methacrylate oxyacetate
18. Titanium acrylate isostearate oxyacetate
19. Titanium dimethacrylate oxyacetate
21. Titanium di(cumylphenylate) oxyacetate
22. Titanium di(dioctylpyrophosphate) oxyacetate
23. Titanium diacrylate oxyacetate
24. Titanium di(butyl, octyl pyrophosphate) di(dioctyl, hydrogen phosphite) oxyacetate
25. Diisostearoyl ethylene titanate
26. Di(dioctylphosphato) ethylene titanate
27. 4-aminobenzenesulfonyl dodecylbenzenesulfonyl ethylene titanate
28. Di(dioctylpyrophosphato) ethylene titanate
29. Di(butyl, methyl pyrophosphato)ethylene titanate di(dioctyl, hydrogen phosphite)
30. Tetraisopropyl di(dioctylphosphito) titanate
31. Tetraoctyloxytitanium di(ditridecylphosphite)
32. Tetra(2,diallyoxymethyl-1 butoxy titanium di(di-tridecyl) phosphite The above listed titanate coupling agents are commercially available.

Illustrative silane coupling agents have the formulas below:

$RSiX_3$
$RR'SiX_2$
$RR'R''SiX$

Where X is Cl, alkoxy of 1–4 carbon atoms (e.g. $OCH_3$, $OC_2H_5$) alkoxy ethers (e.g., $[O(CH_2)_nO(CH_2)_mCH_3]$- where n is 1 to 4, and m is 0 to 4) or $OCH_2CH_2O\ CH_3$ and R, R', R'' are alkyl or substituted alkyls (e.g., of 1 to 20 carbon atoms and allowing for ether linkages), aryls or substituted aryl, (e.g., of 6 to 20 carbon atoms) vinyl, acrylate or methacrylate groups. Substituted alkyls include, but are not limted to:

$NH_2-CH_2CH_2NH-CH_2CH_2CH_2-$

$HS-CH_2CH_2CH_2-$

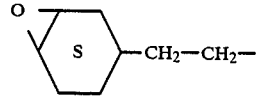

These coupling agents are commercially available.

The particulates or pigments useful in the present invention are preferably finely divided materials having particle sizes of less than 25 microns and preferably less than 10 microns and most preferably less than 2 microns. Suitable materials are non-magentic titanium, iron, aluminum, chromium, copper and cobalt oxides, water insoluble materials such as barium sulfate, a variety of silicates, silica, talcs, carbon black, micas and treated micas, phthalocyanine complexes, and particularly essentially oil and water insoluble cosmetic colorants.

The hydrophobic inner phase for the capsule may be any in situ aminoplast encapsulatable composition as discussed in U.S. Pat. No. 3,516,941. The material or the dispersion produced by incorporation of the particulate may be fluid, semi-solid (e.g., gel), waxy or low melting (less than 100′ C.) solid carrier phase. Typical materials may be fragrance oils, mineral oils, emollients such as isopropyl myristate, plasticizers such as the phthalate esters, waxes such as found in lipsticks, etc.

When the microcapsule is prepared by interfacial polycondensation, the capsule skin may be composed of any condensation polymer or addition polymer, e.g., polyamide, polyurethane, polysulfonamide, polyurea, polyester, polycarbonate, etc. Polyamides prepared by interfacial polycondensation of an amine with an acid chloride or polymers formed by reaction of isocyanate prepolymer with polyamines are preferred. Microcapsules formed by coacervation processes are also useful in forming microcapsule shells according to the present invention. Coacervation is the well known process of forming higher molecular weight gelatin polymers as taught in U.S. Pat. Nos. 2,800,458 and 2,800,457.

The compositions of the present invention are prepared by making the microcapsules and the cosmetic compositions separately and then mixing the two under conditions which will not rupture a significant (e.g., greater than 5% or 10%) portion of the capsules. Preferably, fewer than 1% of the capsules will be broken during preparation of the final composition. In the case of wax or lipid base compositions, intermediate temperatures can be used to soften the compositions prior to mixing with the microcapsules. In powder compositions, the microcapsules and powder can be gently sifted together. In cakes, the pigment and microcapsules may be mixed when dry and then the binder composition added to the mixture. The percentage of capsules and pigments in the composition can vary widely depending on the intensity of the desired effect, the optical intensity of the various pigments, and other aesthetic objectives. Generally, the microcapsules should comprise from 10-90% dry weight of the composition, preferably between 25 and 75% dry weight of the composition. Below are given some particlularly preferred ranges in weight percent of useful components and specifically desired compositions for various cosmetic uses.

| Face Powder (loose): Primary pigment 20–75%, secondary pigment 25–80% | |
|---|---|
| Brilliant lake red (Color Index 15800) | 45% |
| fused silica (flow agent) | 1% |
| Capsule (10–30 microns, 85% payload of ferric ferrocyanide, Color Index 77510 and diethylphthalate) | 54% |
| Face Powder (Compact): Binder (2–25%), primary pigment 20–75%, Microcapsules 78–10% | |
| Carmine (Color Index 75470) | 75% |
| lipid (as binder) | 5% |
| encapsulated titanated mica (glitter) in diethylphthalate | 20% |
| Cream Rouge: 35–65% Cream Base (e.g., water, polyol, lipid, surfactant-emulsifier, preservative and perfume), 15–50% primary pigment, 15–50% microcapsules | |

| -continued | |
|---|---|
| Ultamarine (Color Index 77007) | 35% |
| Cream base | 45% |
| microcapsules (sunset yellow aluminum lake Color Index 15985) in diethylphthalate | 20% |
| Eye Shadow (Compact Powder): 30–70% talc (as powder base), 2–12% metal carboxylate (e.g., zinc stearate) as adherent, 0–3% perfume carrier, 2–10% wax or lipid binder, 0–12% titanium dioxide for covering power, 4–30% primary pigment, and 3–30% microcapsules | |
| talc | 38% |
| zinc stearate | 6% |
| lipid binder | 5% |
| titanium dioxide | 5% |
| primary pigment (ultramarine (Color Index 77007) | 30% |
| microcapsules (litholrubin B, barium lake, Color Index 15850) | 16% |
| Lipstick: 30–70% lipid-wax mixture (e.g., carnauba wax, beeswax), 15–40% lipid solvent (e.g., ricinus oil), 3–15% primary pigment, 3–15% microcapsules | |

The capsules used in these constructions and generally in the practice of the present invention have average diameters between 4 and 100 microns. Preferably the average diameters are between 10 and 80 microns. The capsules preferably constitute from 20 to 60% by volume or weight of the composition layer, most preferably between 25 and 50% by weight or volume of said composition layer.

What is claimed is:

1. A color adjustable cosmetic composition comprising a first colorant, a binder, and frangible mirosapsules comprising a shell, an encapsulated liquid and a second light-stable colorant which differs in color from said first colorant, wherein said second light-stable colorant is on the shell, in the shell, or dispersed in the encapsulted liquid, with a sufficient amount of said second colorant being in the shell or in the encapsulated liquid to cause a visible color change in said cosmetic composition upon rupture of the microcapsules wherein only said second colorant is microencapsulated 2. The composition of claim 1 wherein said second colorant is predominantly in the shell or disperse in the encapsulated liquid.

3. The composition of claim 1 being a compact face powder comprising 2–25% by weight binder, 20–75% by weight first colorant, and 10–80% by weight of microcapsules.

4. The composition of claim 1 being a cream rouge comprising 35–65% cream base, 15–50% first colorant, and 15–50% microcapsules.

5. The composition of claim 1 being a compact eye shadow comprising 30–70% talc, 2–12% metal carboxylate, 2–10% of a binder selected from the group consisting of waxes and lipids, 4–30% first colorant, and 3–30% microcapsules.

6. The composition of claim 5 further comprising up to 12% by weight of a white pigment.

7. The composition of claim 6 wherein said white pigment is titanium dioxide.

8. The composition of claim 6 further comprising a perfume carrier.

9. The composition of claim 7 further comprising a perfume carrier.

10. The composition of claim 1 being a lipstick comprising 30–70% by weight of a binder selected from the group consisting of lipids and waxes, 15–40% by weight of a solvent for said binder, 3–15% by weight of first colorant, and 3–15% by weight of microcapsules.

11. The composition of claim 2 being a compact face powder comprising 2-25% by weight binder, 20-75% by weight first colorant, and 10-80% by weight of microcapsules.

12. The composition of claim 2 being a cream rouge comprising 35-65% cream base, 15-50% first colorant, and 15-50% microcapsules.

13. The composition of claim 2 being a compact eye shadow comprising 30-70% talc, 2-12% metal carboxylate, 2-10% of a binder selected from the group consisting of waxes and lipids, 4-30% first colorant, and 3-30% microcapsules.

14. A process for coloring a surface comprising applying the composition of claim 1 to a surface and subsequently applying pressure to said composition to rupture microcapsules and change the apparent color of the composition.

15. The process of claim 14 wherein said surface is the skin of a human being.

* * * * *

UNITED STATES PATENT AND TRADEMARK OFFICE
CERTIFICATE OF CORRECTION

PATENT NO. : 4,756,906

DATED : July 12, 1988

INVENTOR(S) : NORMAN P. SWEENY

It is certified that error appears in the above-identified patent and that said Letters Patent is hereby corrected as shown below:

Col. 8, line 30, "microsapsules" should read --microcapsules".

Col. 8, line 41, "disperse" should read --dispersed--.

Signed and Sealed this

Sixth Day of June, 1989

Attest:

DONALD J. QUIGG

Attesting Officer

Commissioner of Patents and Trademarks